United States Patent [19]

Huff et al.

[11] Patent Number: 4,923,878
[45] Date of Patent: May 8, 1990

[54] QUINOLIZINE SULFONAMIDES USED AGAINST CERTAIN NEOPLASTIC DISEASE STATES

[75] Inventors: Joel R. Huff, Lederach; Allen I. Oliff, Gwynedd Valley, both of Pa.

[73] Assignee: Merck & Co., Inc., Rahway, N.J.

[21] Appl. No.: 270,323

[22] Filed: Nov. 14, 1988

[51] Int. Cl.⁵ .............................................. A61K 31/44
[52] U.S. Cl. ................................................... 514/285
[58] Field of Search ........................................ 514/285

[56] References Cited

U.S. PATENT DOCUMENTS 4,788,202  11/1988  Ward ................................. 514/285

FOREIGN PATENT DOCUMENTS 2178741A  2/1987  United Kingdom ............... 514/285

OTHER PUBLICATIONS

Cancer Res. 48, 589–601, 2/1988—Shoemaker, et al., Feasibility of Drug Screening with Panels of Human Tumor Cell Lines Using a Microculture Tetrazolium Assay.

Cancer Res. 48, 4827–4833, 9/1988—Shoemaker, et al., Evaluation of a Soluble Tetrazolium/Formazan Assay for Cell Growth and Drug Sensitivity in Culture Using Human and Other Tumor Cell Lines.

Primary Examiner—Jerome D. Goldberg
Attorney, Agent, or Firm—Charles M. Caruso; Hesna J. Pfeiffer

[57] ABSTRACT

Compounds of formula I and its pharmaceutically acceptable salts are formulated with a pharmaceutical carrier for the treatment or prevention of neoplastic diesase states sensitive to such treatment in animals including humans

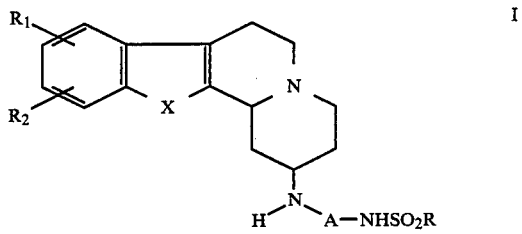

wherein:
A is an alkyl group having 1–6 carbons;
X is oxygen, sulfur, or —NH—;
R is hydrogen or an alkyl group having 1–6 carbons; and
$R_1$ and $R_2$ are independently selected from the group consisting of hydrogen, a halogen a $C_{1-6}$ alkyl group, or $C_{1-3}$ alkoxy.

3 Claims, No Drawings

QUINOLIZINE SULFONAMIDES USED AGAINST CERTAIN NEOPLASTIC DISEASE STATES

BACKGROUND OF THE INVENTION

The present invention relates generally to quinolizine sulfonamides of Formula I and more specifically to benzo[b]furo quinolizine sulfonamides and the use of such compounds in the treatment or prevention of neoplastic disease states sensitive to such treatment in animals including humans.

Pertinent to the background of this invention is United Kingdom Patent Application No. 2178741A which discloses benzo[b] furo-, indol and benzo[b]-thieno quinolizine sulfonamides for use as α-2 adrenoreceptor antagonists in animals. These compounds have been found useful in conditions where antagonism of the α2 adrenoreceptor is desirable, for example as anti depressants, in treatment of diabetes and in inhibiting blood platelet aggregation. However, it has not been known heretofore to use these compounds as anti-neoplastic agents in the treatment or prevention of neoplastic disease states sensitive to such treatment in animals including humans.

SUMMARY OF THE INVENTION

It has now been discovered that quinolizine sulfonamides, in particular (2RS,12bSR)N-[2-((1,3,4, 6,7,12b-hexahydro-2H-benzo[b]furo(2,3-a)quinolizin- 2-yl]-N-2-((methylsulfonyl)ethyl)amine are active as anti-neoplastic agents against certain carcinomas and are particularly effective against renal carcinoma. Thus, it is a purpose of this invention to describe these compounds. It is a further purpose of this invention to describe the anti-neoplastic activity of these compounds. A still further purpose is to describe compositions containing said compounds as the active ingredient thereof. Further purposes will become apparent from a reading of the following description.

DESCRIPTION OF THE INVENTION

In accordance with the present invention a compound of Formula I and its pharmaceutically acceptable salts herein below:

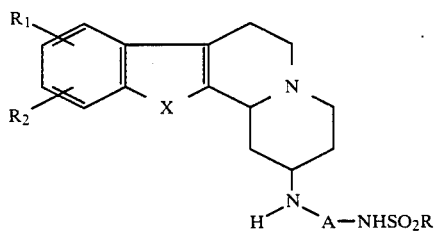

I wherein:
A is an alkyl group having 1-6 carbons;
X is oxygen, sulfur, or -NH-;
R is hydrogen or an alkyl group having 1-6 carbons; and
$R_1$ and $R_2$ are independently selected from the group consisting of hydrogen a halogen, a $C_{1-6}$ alkyl group or $C_{1-3}$alkoxy;
is mixed with a non-toxic pharmaceutical carrier and divided into unit doses, each dose containing an effective neoplasm inhibiting or preventing amount of a compound of Formula I to produce a pharmaceutical composition effective in treating or preventing neoplastic disease states sensitive to such treatment and administering said composition to the animal host having a neoplastic disease states sensitive to such treatment.

The preferred compound of this invention is where A is ethyl, X is oxygen, R is methyl, and $R_1$ and $R_2$ are hydrogen.

The compounds of this invention may be prepared by the procedure set forth in United Kingdom Patent Application No. 2178741A. In the description of the process R, $R_1$, $R_2$, A and X are previously defined. The first step in this process is a reductive amination of a ketone of the general formula;

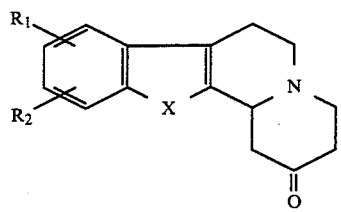

II

This involves reacting the compound of formula II with a diamine of the formula $$NH_2ANH_2$$ 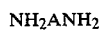 III to form a compound of the formula

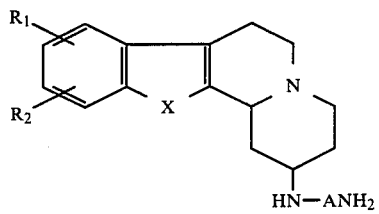

IV

The compound of formula IV is then treated with a reactive derivative of a sulfonic acid having the formula $(RSO_2)_2$, using the requisite amount of reactive derivative for forming a monosulfonamide rather than a disulfonamide. It may be necessary to block one of the amine groups in the diamine of formula IV with a protecting group such as a benzyl, and removing the protecting group after sulfonation.

This results in the formation of a quinolizine sulfonamide of the formula I. The present invention includes all mixtures of the compounds of formula I, especially the racemates, and the dextrorotory and levorotatory enantiomers of these compounds which can be resolved from the racemates.

A neoplastic disease is characterized by an abnormal tissue that grows by cellular proliferation more rapidly than normal tissue and continues to grow after the stimuli that initiated the new growth ceases. Neoplasms show partial or complete lack of structural organization and functional coordination with the normal tissue and usually form a distinct mass of tissue which may be either benign (benign tumor) or malignant (carcinoma).

The therapeutic methods of the present invention comprise the administration of a therapeutically effective amounts of one or more of the compounds of Formula I as an active ingredient together with desired pharmaceutically acceptable diluents, adjuvants and carriers to an animal suffering from a neoplastic disease state sensitive to such treatment or to prevent a neoplastic disease state sensitive to such treatment. A therapeutically effective amount is that amount of the compounds of the present invention needed in order to treat or prevent a neoplastic disease. Unit dosage forms of compound of from 0.1 to 500 mg are administered according to the methods of the invention. Such unit dosage forms may be given to provide a daily dosage of from 1 to 500 mg per kg of body weight of the animal to be treated. Parenteral and oral administration are the preferred routes for practice of the invention methods.

The following example is for illustrative purposes only and are not considered limiting the invention. All temperatures are in °C.

EXAMPLE 1

(2RS,12bSR)-N-[2-(1,3,4,6,7,12b-hexahydro-2H-benzo[b]furo[2,3-a]quinolizin-2-yl)]-N-2-((methanesulfonyl)ethyl)amine Step A: The preparation of (2RS,12bSR)-N-(1,3,4,6,7,12b-hexahydro-2H-benzo[b]furo(2,3-a)quinolizin-2-yl)ethylenediamine To a solution of (12bS)-1,3,4,6,7,12b-hexahydro-2H-benzo[b]furo(2,3-a)quinolizin-2-one (2.41 g, 10 mmol) in 50 ml of THF was added 1.7 ml of 6N HCl solution. After stirring 1 hour the white precipitate was filtered and dried to give 2.7 g of HCL salt which was suspended in 200 ml of isopropanol along with 11 g of 4A° molecular sieves and 2.95 g (49 mmol) of ethylenediamine was added. The reaction was heated for 18 hours, cooled to 0° C. and then 1.05 g (27.6 mmol) of sodium borohydride was added. The temperature was raised to 50° C., stirred for 1 hour and cooled, filtered and concentrated. The residue was diluted with 80 ml of 10% NaOH solution and extracted with ethyl acetate. The organic layer was dried, filtered and concentrated to give 2.64 g of the crude product. This was chromatographed (SiO2, 20% MeOH/NH3 satd. chloroform) to give 2.14 g of pure product.

Step B: The preparation of (2RS,12bSR)-N [2-(1,3,4,6,-7,12b-hexahydro-2H-benzo[b]furo(2,3-a) quinolizin-2-yl)]-N-2-((methylsulfonyl) ethyl)amine To a solution of (2SR,12bSR)-N-(1,3,4,6,7, 12b-hexahydro-2H-benzo[b]furo(2,3-a)quinolizin-2-yl) ethylenediamine (1.2 g, 4 2 mmol) in 50 ml of methylene chloride and 25 ml of water containing 620 mg of potassium carbonate was added 800 mg (4.5 mmol) of methanesulfonic anhydride. This was stirred at room temperature for 2 hours and then diluted with water and extracted with methylene chloride. The organic layer was dried, filtered and concentrated to give the crude product. This was chromatographed to give 1.05 g of product. The dihydrochloride product had a melting point of 276-278° C.

EXAMPLE 2

In Vitro activity of (2RS,12bSR)-N-[2-((1,3,4,6,7,-12b-hexahydro-2H-benzo[b]furo(2,3-a)quinolizin-2-yl]-N-2-((methylsulfonyl)ethyl)amine Tests carried out in accordance with the procedures described in Cancer Research 48, 589-601, February 1988, *Feasibility of Drug Screening with Panels of Human Tumor Cell Lines Using a Microculture Tetrazolium Assay*—Shoemaker et al., and Cancer Research 48, 4827-4833, September 1988, *Evaluation of a Soluble Tetrazolium/Formazan Assay for Cell Growth and Drug Sensitivity in Culture using Human and other Tumor Cell Lines*—Shoemaker et al. A brief description of this procedure follows. For further details refer to the above identified articles.

The procedure was carried out on cell lines from various disease types. Cell lines were maintained as stocks in RPMI 1640 (Quality Biological, Gaithersburg, Md.) supplemented with 10% fetal bovine serum (Sterile Systems, Logon, UT) and 2mM L-glutamine (Central Medium Laboratory, NCI FCRF). Cell cultures were passaged once or twice weekly using trypsin-EDTA (Central Medium Laboratory, NCI-FCRF) to detach the cells from their culture flasks.

Crystalline stock materials of the compound being tested were stored at −70° C. and solubilized in 100% DMSO. The test compound was diluted into complete medium (RPMI 1640 plus fetal bovine serum) plus 0.5% DMSO before addition to cell cultures.

Cellular growth in the presence or absence of the test compound was determined using the MTT-microculture tetrazolium assay. In the MTT assay rapidly growing cells are harvested, counted and inoculated at the appropriate concentrations (100-$\mu$l volume) into 96-well microtiter plates using a multichannel pipet. After 24 hours the test compound is applied (100-$\mu$l volume) to triplicate culture wells and cultures were incubated for 6 days at 37° C. MTT (Sigma, St. Louis, MO) is prepared at 5 mg/ml in PBS (Dulbeccs and Vogt formulation, without calcium and magnesium; (Quality Biological, Gaithersburg, Md.) and stored at 4° C. On Day 7, MTT was diluted 1 to 5 in medium without serum and 50 $\mu$l were added to microculture wells. After 4 hours incubation at 37° C., 250 $\mu$l were removed from each well and 150 $\mu$l of 100% DMSO were added to solubilize the MTT formazan product. After thorough mixing with a mechanical plate mixer, absorbance at 540 nm was measured with a Dynatech model MR600 microplate reader. (2RS,12bSR)-N-[2-((1,3,4,6,7,12b -hexahydro-2H-benzo[b]furo(2,3-a)quinolizin-2-yl]-N-2-((methylsulfonyl)ethyl)amine is shown to selectively inhibit the growth of cell lines derived from renal carcinomas at the indicated concentrations.

| Cell Line | IC$_{50}$ |
|---|---|
| Renal | |
| A704 | 0.16 $\mu$M |
| A498 | 1.6 $\mu$M |
| SN-12KI | 6.3 $\mu$M |

What is claimed is:

1. A method of treating or preventing neoplastic disease in animals including humans which comprises administering a therapeutically effective amount of a compound of the formula:

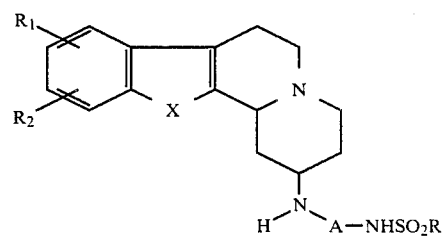

wherein:
  A is ethylene;
  X is oxygen;
  R is methyl;
  $R_1$ and $R_2$ are hydrogen; and the pharmaceutically acceptable salts thereof to an animal affected by neoplastic disease which is sensitive to treatment with the compounds of formula I.

2. A method of treating or preventing neoplastic disease in animals including humans which comprises administering a therapeutically effective amount of (2Rs,12bSR)-N-[2-((1,3,4,6,7,12b-hexahydro-2H-benzo[b]furo(2,3-a) quinolizin-2-yl)]-N-2-((methyl-sulfonyl)ethyl)amine to an animal affected by neoplastic disease which is sensitive to treatment with this compound.

3. A method according to claim 2 wherein the amount of the (2RS,12bSR)-N-[2-((1,3,4,6,7,12b-hexahydro-2H-benzo[b]furo(2,3-a) quinolizin-2-yl)]-N-2-((methylsulfonyl)ethyl)amine administered comprises a dose of from about 1 to 500 mg per kg of the body weight per day.

* * * * *